United States Patent [19]

Kreh

[11] Patent Number: 4,701,245
[45] Date of Patent: Oct. 20, 1987

[54] OXIDATION OF ORGANIC COMPOUNDS USING A CATALYZED CERIUM (IV) COMPOSITION

[75] Inventor: Robert P. Kreh, Jessup, Md.

[73] Assignee: W. R. Grace & Co., New York, N.Y.

[21] Appl. No.: 942,758

[22] Filed: Dec. 17, 1986

Related U.S. Application Data

[63] Continuation-in-part of Ser. No. 859,548, May 5, 1986, Pat. No. 4,639,298, and Ser. No. 917,462, Oct. 10, 1986.

[51] Int. Cl.[4] .................................... C07C 50/12
[52] U.S. Cl. ............................. 204/78; 204/59 R; 260/369; 260/385
[58] Field of Search .............. 204/78, 59 R; 260/369, 260/385

[56] References Cited

U.S. PATENT DOCUMENTS

| | | | |
|---|---|---|---|
| 808,095 | 12/1905 | Lang | 204/78 |
| 3,413,203 | 11/1968 | MacLean | 204/79 |
| 3,486,992 | 12/1969 | Frye | 204/86 |
| 3,873,580 | 3/1975 | Rennie | 260/362 |
| 4,212,710 | 7/1980 | Halter et al. | 204/78 |
| 4,212,711 | 7/1980 | Halter et al. | 204/78 |
| 4,312,721 | 1/1982 | Oehr | 204/78 |
| 4,313,804 | 2/1982 | Oehr | 204/93 |
| 4,354,904 | 10/1982 | Malloy et al. | 204/59 R |
| 4,371,431 | 2/1983 | Switzer et al. | 204/59 R |
| 4,387,007 | 6/1983 | Seiler | 204/59 R |
| 4,482,438 | 11/1984 | Ballard et al. | 204/78 |
| 4,530,745 | 7/1985 | Komatsu et al. | 204/130 |
| 4,536,337 | 8/1985 | Komatus et al. | 204/396 R |
| 4,560,804 | 12/1985 | Yeh et al. | 568/408 |
| 4,582,942 | 4/1986 | Comninellis et al. | 568/426 |
| 4,624,757 | 11/1986 | Lysenko et al. | 204/73 R |
| 4,624,759 | 11/1986 | Lysenko et al. | 204/73 R |
| 4,632,782 | 12/1986 | Komatsu et al. | 260/385 |
| 4,639,298 | 1/1987 | Kreh et al. | 260/385 |
| 4,647,349 | 3/1987 | Kreh et al. | 260/385 |

FOREIGN PATENT DOCUMENTS

| | | |
|---|---|---|
| 899856 | 5/1972 | Canada. |
| 1132996 | 10/1982 | Canada. |

OTHER PUBLICATIONS

J. Org. Chem. (1983) vol. 48, pp. 1487–1491 by M. Marrocco et al., Prospects for the Indirect Electrolytic Oxidation of Organics by Ibl et al., Electro-Organic Synthesis Technology, No. 185, vol. 75 (1979) pp. 45–50.
Performance of Two-Phase Electrolyte Electrolysis by H. Feess et al., Techniques of Chemistry, vol. V, Part III, Ed. by N. L. Weinberg et al., pp. 104–176.

*Primary Examiner*—Arthur P. Demers
*Attorney, Agent, or Firm*—Howard J. Troffkin

[57] ABSTRACT

A process for oxidizing aromatic and alkyl substituted aromatic compounds to quinonoid compounds by contacting an aromatic and alkyl aromatic compound with an acidic, aqueous solution of ceric oxidant in the presence of a catalytic amount of chromium cations. The present process provides a means of forming the desired quinonoid product in good yields and high selectivity.

31 Claims, No Drawings

OXIDATION OF ORGANIC COMPOUNDS USING A CATALYZED CERIUM (IV) COMPOSITION

This application is a continuation-in-part of copending U.S. application having Ser. No. 859,548, filed May 5, 1986, now U.S. Pat. No. 4,639,298, and U.S. application having Ser. No. 917,462, filed Oct. 10, 1986.

BACKGROUND OF THE INVENTION

The present invention is directed to an improved electrochemical oxidation process for forming quinonoid from corresponding aromatic and alkyl aromatic compounds in good yields and high selectivity. More specifically, the invention described and claimed herein requires the use of an aqueous, acidic solution containing ceric oxidant in the presence of a catalytic amount of chromium cations.

The quinones obtainable by the present process have a wide variety of known utility. For example, naphthoquinone, is a known additive in the paper making industry. Other quinones are useful as intermediates in forming fragrance components for perfumes as well as in forming pharmaceuticals. The products achieved by the present invention have been previously formed by a variety of processes which may be generally classified as chemical or electrochemical. Oxidation of aromatic compounds has been achieved by direct electrochemical oxidation in the presence of dilute acid electrolytic solutions as described in U.S. Pat. Nos. 4,298,438 and 4,354,904 as well as by indirect electrochemical oxidation in which the oxidant is electrolytically generated and, in turn, used to oxidize the aromatic compound.

Compounds which are known to be capable of acting as an indirect oxidant include the polyvalent metal salts, particularly the metals of cobalt, chromium, manganese, iron, lead, silver and cerium. Because regeneration of the spent metal to its higher oxidation state is not always highly effective and/or other insoluble salts are formed, those skilled in this art tend to use the salts of chromium, manganese, cobalt, iron or lead as these salts are less expensive and replacement of spent materials do not greatly detract from the economics of the process. However, each of these metal ion oxidants have certain properties which cause them to make the oxidation process ineffective. For example, chromium ions, when used as the sole oxidant, exhibits low reactivity and poor selectivity towards the desired products, cerium and manganese salts are believed to have low reactivity either as the oxidant or with respect to regeneration of the oxidant specie, the higher oxidation states of silver, cobalt and lead ions are not very stable and, in the case of iron, is not very reactive.

The ceric ion is a well known oxidizing agent in organic chemistry. It has the potential of presenting an excellent one electron oxidant but has not been previously used extensively or on an industrial scale because it has been associated with poor reactivity and selectivity. The cerium salts are prohibitively expensive and must, therefore, be capable of being stable, react with the organic substrate cleanly and be easily regenerated to its higher valence state. For an effective industrial process it is desirable to produce the product in a high yield based on substrate and the oxidant. This has been difficult to accomplish for some products, such as 2-methyl-1,4-naphthoquinone. West German patent No. 2952709 describes the production of 2-methyl-1,4-naphthoquinone from 2-methylnaphthalene using $CrO_3$ in aqueous $H_2SO_4$. While the yield based on substrate was 71%, the yield based on $CrO_3$ was only 17%. Japanese patent No. 60/252445 shows the same oxidation using $Ce(SO_4)_2$ in aqueous sulfuric acid as the oxidant. The yield was 24% based on substrate and 47% based on Ce(IV).

Canadian Patent No. 1,132,996 to Oehr describes a process for oxidizing naphthalene to naphthaquinone using ceric sulfate in dilute sulfuric acid. The low solubility limitations of cerium sulfate [Solubilities of Inorganic and Organic Compounds, Vol. 3, Part I, Ed. by H. L. Silcock (1974)]cause low efficiency and low yields as well as the need for large volumes of solution to oxidize small quantities of the organic compound.

It must be understood that although cerous/ceric ions have been known and used in oxidation reactions, there is a need to enhance the system to provide a commercially attractive process. The present process provides a catalyzed system which causes the cerium to be highly selective in forming the desired quinonoid compounds, to be capable of exhibiting high reaction rates and yield and to be capable of undergoing repeated cycling between its cerous ($Ce^{+3}$) and ceric ($Ce^{+4}$) species in a high degree of efficiency under the reaction and electrolysis conditions to make the process attractive on a commercial scale.

SUMMARY OF THE INVENTION

The present invention is directed to an electrochemical process wherein ceric ions are generated and used as an oxidant to transform aromatic and alkyl substituted aromatic compounds to quinonoid compounds in enhanced yield and selectivity. The present process requires the utilization of cerium salts in an acidic aqueous solution containing a catalytic amount of chromium cations therein.

DETAILED DESCRIPTION OF THE INVENTION

The present invention is directed to a process for selectively forming quinone compounds from respective aromatic compounds.

Certain terms used in the present specification and in the appended claims are defined hereinbelow to aid in providing a clear description of the invention:

The term "aromatic" shall, unless specifically indicated otherwise, refer to benzylic and fused benzylic compounds such as benzene, naphthalene, anthracene and the like. The compounds may be unsubstituted or may contain substitution groups which are inert to oxidation such as halides, alkoxy, nitro, sulfonyl, amide, tertiary amino, tertiary akyl and carboxylate ester groups.

The term "alkyl aromatic" refers to $C_1$–$C_6$ alkyl substituted benzylic and fused benzylic compounds. The compounds shall contain one or more than one primary or secondary $C_1$–$C_6$ alkyl group attached to the aromatic ring and may, in addition, contain groups which are inert to oxidation such as halides, alkoxy, nitro, sulfonyl, amido, tertiary amino, tertiary alkyl, and carboxylic ester groups. Examples of such compounds include toluene, (o, m or p) xylene, trimethylbenzene, (o, m or p) ethyltoluene, (o, m or p) propyltoluene, (o, m or p) methoxyethylbenzene, (o, m or p) ethoxyethylbenzene, 1, 2 dimethylnaphthalene, (o, m or p) methyl-N,N-dimethylaniline (o, m or p) chlorotoluene and the like.

The term "indirect electrochemical oxidation" refers to an oxidation of an aromatic or alkyl aromatic compound which proceeds in two steps such that the first step provides a metal ion oxidant (e.g. $Ce^{+4}$) by anodic charge exchange and the second step comprises the reacting of the metal ion oxidant with an aromatic or alkyl aromatic compound to produce carbonyl containing compounds. The oxidation of the aromatic or alkyl aromatic compound does not occur selectively in the absence of the metal ion oxidant. The indirect electrochemical oxidation of the organic substrate can be conducted in the electrochemical reactor (in-cell) or in a separate reactor (ex-cell).

The terms "cerous", "ceric" and "cerium" refer, respectively to the cerium ion or salt of a cerium ion in its lower valence state (+3), its higher valence state (+4) and as a mixture of both lower and higher valence state species.

The terms "chromium cations" shall refer to chromium ions or salts of chromium ions in any of its plus two, plus three and plus six valence states as well as mixtures of said species.

The product of the present process are cyclic diones having the so-called quinonoid structure. The term "quinone" and "quinonoid" as used herein and in the appended claims refers to cyclic diones. These compounds can be viewed as having two C=O groups in which each carbon is part of the cyclic ring structure. The diones can be positioned ortho or para to each other and include, for example, para-benzoquinone, ortho-benzoquinone, 1,2-, 1,4, and 2,6-naphthaquinone, acenaphthaquinone, anthraquinone and the like.

The present invention provides an improved indirect electrochemical oxidation process to produce quinonoid compounds. The improvement requires the utilization of an aqueous acidic solution of cerium salts in the presence of a catalytic amount of chromium cations to oxidize an aromatic or alkyl substituted aromatic compound to its related quinone species. In a preferred embodiment, the cerium salt is cerium methanesulfonate in an aqueous solution containing free methanesulfonic acid.

The present invention provides a means of enhancing indirect electrochemical oxidation processes in which cerium is used as the oxidant. Any known cerium salt can be used to provide the ceric oxidant specie. The ceric specie is generated by anodic electrochemical method in manners well known to those skilled in the art. The cerium salts include nitrates, perchlorates, halides such as chloride, fluoride, etc., sulfate, acetate, boron fluoride, silicon fluoride, methanesulfonate, trifluoromethanesulfonate and the like. The cerium salts which are preferred are the sulfate, acetate, nitrate, methanesulfonate and trifluoromethanesulfonate because the anions of these salts are less reactive with the organic substrate. These cerium salts can be utilized in concentrations of at least about 0.1 molarity and preferably from about 0.5 to about 1.5 molarity. Normally they have been utilized at low concentrations to enhance the retention of the salt in solution or they are used as a slurry due to the solubility characteristics of either the ceric or cerous specie or both. U.S. applications having Ser. No. 859,548, filed May 5, 1986 and Ser. No. 917,462, filed Oct. 10, 1986, now U.S. Pat. No. 4,639,298 (the teachings of which are incorporated herein by reference) describe a means of using high concentrations of cerium methanesulfonate and cerium trifluoromethanesulfonate dissolved in an aqueous solution containing free methanesulfonic acid or trifluoromethanesulfonic acid therein to provide an effective oxidant system for indirect electrochemical synthesis. The most preferred cerium salts used as the oxidant in the present process are cerium methanesulfonate, cerium trifluoromethanesulfonate or mixtures thereof. These salts can be used alone or in combination with other cerium salts described above.

Cerium salts can be used as an effective oxidant for indirect electrochemical synthesis. Cerium methanesulfonate has been found capable of remaining dissolved in the process solution to provide an effective cerium salt oxidant. This can be achieved by having the aqueous solution contain at least 1.5 and preferably at least 2 Normal concentration of free methanesulfonic acid with respect to the cerous ion concentration present at any point in the system. Alternately, at low concentrations of free acid, high selectivity can be maintained by utilizing an aqueous-organic missible cosolvent system.

The oxidation of certain organic substrates using ceric oxidant has been found to be enhanced by the presence of a catalytic amount of chromium cations. Although chromium itself has been used as an oxidant because of its multivalence states, it is known as a very ineffective oxidant and the enhanced results presently achieved can not be attributed to the additive effective of the ceric and chromium cations present in the present system. The presence of catalytic amounts of chromium cations to a ceric oxidant system has been unexpectedly found to provide enhanced yield and/or selectivity of the quinone product. When alkyl substituted fused ring systems are used as the organic substrate, the yield of the preferred quinone obtained under conventional process conditions is normally enhanced when formed according to the present invention. For example, 2-methylnaphthalene yields 2-methylnaphthaquinone in substantially higher yields using the present process than is achievable when using only the same cerium salt alone. It is believed that alkyl substituted aromatics provide greater yields of the related quinone derivative over the aldehyde or ketone derivative.

The chromium cation can be introduced by the presence of any chromium salt which is soluble in the acidic solution of the process. Such salts include the chromium oxides, including the mono, di and trioxides, sulfate, nitrate, halides, in particular the chloride and bromide, acetate, phosphate and the like.

The chromium cation can be introduced in any of its positive valencies which are the plus two, plus three or plus six valence state. The chromium cation should be present in the system in a catalytic amount with respect to the cerium ions present in the system. The chromium to cerium molar ratio can range from about 1:600 to 1:20 with a range of from 1:150 to 1:30 being preferred. The presence of large amounts of chromium in the system should be avoided as the yield of quinone product is drastically reduced under such conditions.

The present process is carried out in an acidic aqueous solution. The acid can be selected from any water soluble organic or inorganic acid and is preferably selected from the corresponding free acid of the cerium salt being employed. For example, when cerium sulfate is used it is preferred to use an aqueous solution having sulfuric acid therein. In one of the preferred embodiments of the present invention cerium methanesulfonate is used in an aqueous solution having at least 1.5 Normal free methanesulfonic acid therein or having lower amounts of the free acid in combination with an organic cosolvent.

The solution can contain an organic cosolvent which is at least partially miscible with water. The organic compound should be at least 2, preferably at least 5 percent (on a weight basis) soluble with water. Such material must be substantially inert under the conditions encountered in the present process. The cosolvent must, therefore, be substantially inert with respect to the acidic and redox conditions of the process. Compounds which are most suitable as the organic cosolvent include nitriles such as acetonitrile, propionitrile, butyronitrile and the like; nitroalkanes such as nitromethane and nitroethane; alkoxy compounds such as dimethyl ether, diethyl ether, methylene dimethyl ether, methylene diethyl ether, tetrahydrofuran, 1,2-dimethoxyethane and the like; sulfonyl containing compounds such as dimethyl sulfone, tetramethyl sulfone (sulfolane), diethyl sulfone and the like; sulfoxides, such as dimethyl sulfoxide and the like; amides such as N-methyl pyrrolidone, dimethylformamide, 2-pyrrolidone and the like; organic carbonates, such as propylene carbonate and the like; alcohols such as methanol, ethanol, t-butanol and the like; ketones such as acetone, methyl ethyl ketone and the like; their equivalents as well as mixtures thereof. The most preferred organic cosolvents are $C_1$-$C_3$ alkyl nitriles, especially acetonitrile, and $C_1$-$C_2$ nitroalkanes. The organic cosolvent can be present as part of the system in from 2 percent to about 50 percent. It can be introduced into the system as part of the aromatic or alkyl aromatic feed (especially in a batch process) or introduced separately to form the aqueous phase of the process. Other conventional materials may be added to the system provided they are inert to the cerium salt and free acid used herein. Examples of such materials include anionic surfactants such as sodium dodecylbenzene sulfonate and the like and cationic surfactants such as tetrabutylammonium hydroxide and the like.

The generation and subsequent regeneration of ceric oxidant can be readily carried out by supplying the solution of the present invention to an electrolytic cell in either a batch or continuous manner. The cell may be either undivided or divided by a porous partition wall or membrane between electrodes. The electrodes may be of any suitable form such as plates, lattices, expanded metal, or reticulated porous material and the like. The anode may be any of the known materials suitable for preforming the metal-ion oxidation and are, preferably selected from lead, lead oxide, platinum, platinized titanium, platinized niobium or metal oxide-titanium composite. The cathode of the cell may be any of the known materials suitable for performing reductions in the aqueous-acid solutions with or without the presence of metal ions such as, for example, steel, copper, and nickel. The use of the presently described process has, as one of its unexpected properties, the ability to readily and effectively generate and regenerate ceric oxidant from cerous ions at high current density. Another unexpected property is the ability to cause a clean cathodic reduction without production of by-products or chromium base metal which detract from the process and require separation therefrom. The electrolysis can be performed at voltages ranging from about 2 to 20 volts with current density ranging between about 0.1 to about 500 mA/cm$^2$, preferably from 10 to 400 mA/cm$^2$ and most preferably from 30 to 300 mA/cm$^2$ (based on electrode area excluding roughness factor). The electrolysis may be conducted at a temperature of from about $-20°$ to 150° C. and preferably from 0° to 100° C. It is most preferable to have the cell temperature and the reaction temperature (where the cell and chemical reactor are separate) be substantially the same.

The organic compounds which can be effectively oxidized using the solution of the present process are aromatic and alkyl aromatic compounds. The aromatic compounds include benzylic and fused benzylic ring compounds which may be unsubstituted or be substituted with a group which is substantially inert to oxidation. Examples of such compounds include benzene, naphthalene, anthracene and the like as well as such compounds which contain groups attached to the ring which are inert to the present indirect oxidation. Such groups can be readily determined by simple laboratory testing and include ($C_1$-$C_4$) alkoxy, tert-alkyl ($C_4$-$C_7$), phenoxy, nitro, tertiary amino, sulfonyl, amido, and carboxylic acid ester groups and the like. The alkyl substituted aromatic compounds include the above defined aromatic compounds which further contains at least one primary alkyl or secondary alkyl group or both.

The organic compounds described above are oxidized to their respective quinonoid compounds by contacting the organic compound with the acidic aqueous solution described above which contains the catalysed ceric oxidant. The contacting of the oxidant and the organic compound may be conducted directly within the electrolytic cell. However, it is preferable to transfer the subject oxidant containing solution to a separate reactor vessel where it is contacted with the organic compound to be oxidized under agitation. The organic compound can be introduced to the reactor either dissolved or dispersed in the aqueous phase or dissolved in a co-solvent with the aqueous solution.

The organic oxidation can be carried out under ambient temperature and pressure conditions. The temperature may be varied from about 0° to about 100° C. with from 20° to 75° C. being preferred. The pressure may be elevated or reduced for process reasons.

The solution removed from the reaction zone contains product and spent metal ion oxidant (cerous). The product can be readily separated from the solution by phase-separation, distillation, precipitation or extraction with an appropriate solvent such as dichloroalkanes, cyclohexane and the like. The particular mode of separation will depend upon the identity of the product formed and can be readily ascertained by the artisan.

The resultant solution (after separation of the product) will contain cerous salt as the sole or major component and may contain small amounts of unreacted ceric salt in addition to chromium cations. This solution can be returned to the electrolytic cell for regeneration of the ceric ion oxidant. It has been found that the ceric/cerous salts used herein readily regenerate a multiplicity of cycles without formation of by-products which have detrimental effect on the efficiency of the process.

The following examples are given for illustrative purposes only and are not meant to be a limitation on the present invention as defined by the claims appended hereto. All parts and percentages are by weight unless otherwise indicated.

EXAMPLE 1

To 83 parts by volume of 0.73 cerium(IV) methanesulfonate and 2.8M $CH_3SO_3H$ in water was added 0.1 part of $CrO_3$ in 60 parts by volume of water. This solution was heated to 75° C. and purged with nitrogen, and then 1.42 parts of 2-methylnaphthalene in 30 parts by volume of 1,2-dichloroethane were added. The mixture was stirred vigorously at 75° C. and 30 parts by volume of acetonitrile were added. After 30 minutes, the mixture was extracted with 300 parts by volume of methylene chloride. Quantitative analysis by gas chromatography showed 0.11 part 2-methylnaphthalene and 0.98 part 2-methyl-1,4-naphthoquinone (65% yield based on the substrate; 54% yield based on the oxidant) and 0.26 part 6-methyl 1,4-naphthoquinone (17% yield based on the substrate; 14% yield based on oxidant). Note that the desired product was 2-methyl-1,4-naphthoquinone (menadione).

EXAMPLE 2

This example is given for comparative purposes only. The procedure of example 1 was repeated except that the $CrO_3$ was omitted, yielding at the end of 30 minutes, 0.09 part 2-methylnaphthalene, 0.85 part 2-methyl-1,4-naphthoquinone (55% yield based on substrate; 48% yield based on oxidant) and 0.27 part 6-methyl-1,4-naphthoquinone (18% yield based on substrate; 16% yield based on oxidant).

What is claimed:

1. A process for forming quinonoid group containing compounds from their respective organic substrate selected from aromatic and alkylaromatic compounds comprising contacting the organic substrate with an aqueous acidic solution containing ceric ions in the presence of a catalytically effective amount of chromium cations, said solution having at least about 0.1 molar cerium concentration therein.

2. The process of claim 1 wherein the concentration of chromium and cerium in said aqueous acidic solution is such that the chromium to cerium molar ratio is from 1:600 to 1:20.

3. The process of claim 1 wherein the cerium salt is selected from the group consisting essentially of cerium sulfates, cerium acetates, cerium nitrates, cerium methanesulfonate, cerium trifluoromethanesulfonate and mixtures thereof.

4. The process of claim 2 wherein the cerium salt is selected from the group consisting essentially of cerium sulfates, cerium acetates, cerium nitrates, cerium methanesulfonate, cerium trifluoromethanesulfonate and mixtures thereof.

5. The process of claim 1 wherein the cerium salt is selected from cerium methanesulfonate, the aqueous acidic solution contains at least 1.5 molar concentration of free methanesulfonic acid and the cerium concentration is at least 0.2 molar.

6. The process of claim 2 wherein the cerium salt is selected from cerium methanesulfonate, the aqueous acidic solution contains at least 1.5 molar concentration of free methanesulfonic acid and the cerium concentration is at least 0.2 molar.

7. The process of claim 1 wherein the aqueous acidic solution further contains an organic cosolvent, said cosolvent being at least partially miscible in the aqueous solution.

8. The process of claim 2 wherein the aqueous acidic solution further contains an organic cosolvent, said cosolvent being at least partially miscible in the aqueous solution.

9. The process of claim 5 wherein the aqueous acidic solution further contains an organic cosolvent, said cosolvent being at least partially miscible in the aqueous solution.

10. The process of claim 1 wherein the substrate is 2-methylnaphthalene.

11. The process of claim 2 wherein the substrate is 2-methylnaphthalene.

12. The process of claim 5 wherein the substrate is 2-methylnaphthalene.

13. The process of claim 7 wherein the substrate is 2-methylnaphthalene.

14. The process of claim 1 wherein the cerium salt is selected from cerium methanesulfonate, cerium trifluoromethanesulfonate or mixtures thereof, the aqueous acidic solution contains from about 0.01 to 1.3 molar concentration of an acid selected from methanesulfonic acid, trifluoromethanesulfonic acid or mixtures thereof and said solution contains an organic cosolvent which is substantially inert and is at least partially miscible in the aqueous solution.

15. The process of claim 7 wherein the organic cosolvent is selected from a $C_1$–$C_3$ alkyl nitrile, a $C_1$–$C_2$ nitroalkane, and mixtures thereof.

16. The process of claim 14 wherein the organic cosolvent is selected from a $C_1$–$C_3$ alkyl nitrile, a $C_1$–$C_2$ nitroalkane, and mixtures thereof.

17. An indirect electrochemical oxidation process to oxidize aromatic and alkyl aromatic compounds comprising
   (a) contacting an organic substrate selected from aromatic and alkyl aromatic compounds with an aqueous acidic solution containing ceric oxidant in the presence of a catalytically effective amount of chromium cations, said solution having at least about 0.1 molar cerium concentration;
   (b) separating and recovering the quinonyl product from the solution to yield a spent solution rich in cerous salts;
   (c) transferring the spent solution to an electrochemical cell to cause regeneration of a solution rich in the ceric salt; and
   (d) repeating steps (a), (b) and (c).

18. The process of claim 17 wherein the aqueous solution contains chromium and cerium therein in a molar ration of from 1:600 to 1:20.

19. The process of claim 17 wherein the cerium salt is selected from the group consisting essentially of cerium sulfates, cerium acetates, cerium nitrates, cerium methanesulfonate, cerium trifluoromethanesulfonate and mixtures thereof.

20. The process of claim 18 wherein the cerium salt is selected from the group consisting essentially of cerium sulfates, cerium acetates, cerium nitrates, cerium methanesulfonate, cerium trifluoromethanesulfonate and mixtures thereof.

21. The process of claim 17 wherein the cerium salt is selected from cerium methanesulfonate, the aqueous acidic solution contains at least 1.5 molar concentration of free methanesulfonic acid and the cerium concentration is at least 0.2 molar.

22. The process of claim 18 wherein the cerium salt is selected from cerium methanesulfonate, the aqueous acidic solution contains at least 1.5 molar concentration of free methanesulfonic acid and the cerium concentration is at least 0.2 molar.

23. The process of claim 21 wherein the aqueous acidic solution further contains an organic cosolvent, said cosolvent being at least partially miscible in the aqueous solution.

24. The process of claim 22 wherein the aqueous acidic solution further contains an organic cosolvent, said cosolvent being at least partially miscible in the aqueous solution.

25. The process of claim 17 wherein the cerium salt is selected from cerium methanesulfonate, cerium trifluoromethanesulfonate or mixtures thereof, the aqueous acidic solution contains from 0.01 to 1.3 molar concentration of an acid selected from methanesulfonic acid, trifluoromethanesulfonic acid or mixtures thereof and said solution contains an organic cosolvent which is substantially inert and is at least partially miscible in the aqueous solution.

26. The process of claim 17 wherein the substrate is 2-methylnaphthalene.

27. The process of claim 19 wherein the substrate is 2-methylnaphthalene.

28. The process of claim 21 wherein the substrate is 2-methylnaphthalene.

29. The process of claim 23 wherein the substrate is 2-methylnaphthalene.

30. The process of claim 25 wherein the substrate is 2-methylnaphthalene.

31. The process of claim 17 wherein step (a) is conducted at a temperature of from about 0° C. to 100° C. and the electrolysis of step (c) is conducted at a cell voltage ranging from about 2 to 20 volts with a current density of from 10 to 400 mA/cm$^2$.

* * * * *